(12) United States Patent
Woodbury et al.

(10) Patent No.: US 8,318,413 B2
(45) Date of Patent: Nov. 27, 2012

(54) AMNIOPUNCH AND USES THEREOF

(75) Inventors: Dale Woodbury, Middletown, NJ (US); Akiva Marcus, Teaneck, NJ (US)

(73) Assignee: The University of Medicine and Dentistry of New Jersey, Somerset, NJ (US)

( * ) Notice: Subject to any disclaimer, the term of this patent is extended or adjusted under 35 U.S.C. 154(b) by 533 days.

(21) Appl. No.: 12/332,256

(22) Filed: Dec. 10, 2008

(65) Prior Publication Data
US 2009/0202976 A1    Aug. 13, 2009

Related U.S. Application Data

(60) Provisional application No. 61/007,130, filed on Dec. 11, 2007.

(51) Int. Cl.
*A01N 1/00* (2006.01)
(52) U.S. Cl. ........................ 435/1.1; 435/284.1
(58) Field of Classification Search ............ 435/309.1; 600/562–572, 573–584, 588, 591, 304, 351; 606/167–189
See application file for complete search history.

(56) References Cited

U.S. PATENT DOCUMENTS

| | | | |
|---|---|---|---|
| 4,681,123 A | 7/1987 | Valtchev | |
| 6,659,338 B1 * | 12/2003 | Dittmann et al. | 235/375 |
| 2005/0059041 A1 * | 3/2005 | Johnson et al. | 435/6 |
| 2007/0021684 A1 * | 1/2007 | Brielmeier et al. | 600/564 |
| 2007/0100361 A1 | 5/2007 | Cohen | |
| 2007/0148724 A1 * | 6/2007 | Salter et al. | 435/32 |

FOREIGN PATENT DOCUMENTS

| | | | |
|---|---|---|---|
| WO | WO 2007013820 A1 * | 2/2007 | |
| WO | WO 2007079754 A1 * | 7/2007 | |

OTHER PUBLICATIONS

Branski et al, Amnion in the treatment of pediatric partial-thickness facial burns. Burns (2008) 34:393-399.
Espana et al, Amniotic membrane transplantation for bullous keratopathy in eyes with poor visual potential. J Cataract Refract Surg (2003) 29:279-284.
Georgiadis et al, Cryopreserved amniotic membrane transplantation for the management of symptomatic bullous keratopathy. Clin Experiment Ophthalmol (2008) 36:130-135.
Ilancheran et al, Human fetal membranes: a source of stem cells for tissue regeneration and repair? Placenta (2009) 30:2-10.
Ilancheran et al, Stem cells derived from human fetal membranes display multilineage differentiation potential. Biology of Reproduction (2007) 77:577-588.
Koziak et al, Reconstructive surgery of male urethra using human amnion membranes (grafts)—first announcement. Ann Transplant (2004) 9:21-24.
Marcus et al, Isolation, characterization, and differentiation of stem cells derived from the rat amniotic membrane. Differentiation (2008) 76:130-144.
Marcus and Woodbury, Fetal stem cells from extra-embryonic tissues: do not discard. J Cell Mol Med (2008) 12:730-742.
Mhaskar, Amniotic membrane for cervical reconstruction. Int J Gynaecol Obstet (2005) 90:123-127.
Miki et al, Stem cell characteristics of amniotic epithelial cells. Stem Cells (2005) 23:1549-1559.
Miki et al, Identification of stem cell marker-positive cells by immunofluorescence in term human amnion. J Reprod Immunol (2007) 75:91-96.
Niknejad et al, Properties of the amniotic membrane for potential use in tissue engineering. Eur Cell Mater (2008) 15:88-99.
Park et al, Clinical efficacy of amniotic membrane transplantation in the treatment of various ocular surface diseases. Cont Lens Anterior Eye (2008) 31:73-80.
Park et al, Healing of a porcine burn wound dressed with human and bovine amniotic membranes. Wound Repair Regen (2008) 16:520-528.
Sangwan et al, Amniotic membrane transplantation: a review of current indications in the management of ophthalmic disorders. Indian J Ophthalmol (2007) 55:251-260.
Sonmez et al, Amniotic membrane transplantation with anterior stromal micropuncture for treatment of painful bullous keratopathy in eyes with poor visual potential. Cornea (2007) 26:227-229.
Sridhar et al, Amniotic membrane transplantation in acute chemical and thermal injury. Am J Ophthalmol (2000) 130:134-137.
Takahashi et al, Immunohistochemical observation of amniotic membrane patching on a corneal alkali burn in vivo. Jpn J Ophthalmol (2007) 51:3-9.
Tejwani et al, Role of amniotic membrane graft for ocular chemical and thermal injuries. Cornea (2007) 26:21-26.
International Search Report issued on Feb. 5, 2009, in related Application No. PCT/US08/86280.

* cited by examiner

*Primary Examiner* — Allison Ford
*Assistant Examiner* — Paul D. Pyla
(74) *Attorney, Agent, or Firm* — Reed Smith LLP

(57) ABSTRACT

A tissue, such as an amniotic or chorionic membrane, harvesting device that integrates a system facilitating subsequent storage of tissue samples. The device cuts a sample of the target tissue and automatically deposits the sample in a storage vessel. A method of collecting and storing a sample from a target tissue using a tissue harvesting device. A kit for collecting and storing samples of the target tissue.

18 Claims, 9 Drawing Sheets

Direction of Movement

Direction of Movement

AMNIOPUNCH AND USES THEREOF

CROSS-REFERENCE TO RELATED APPLICATIONS

This application claims priority from U.S. Provisional Application Ser. No. 61/007,130, filed on Dec. 11, 2007, which is incorporated herein by reference in its entirety.

FIELD OF THE INVENTION

The present invention relates to a device and methodology for generating tissue samples from biological materials.

BACKGROUND

During gestation the fetus develops within the confines of the gestational sac. A pair of juxtaposed, resilient membranous structures define the outer margins of the gestational sac: an inner amniotic membrane (amnion) and an outer chorionic membrane (chorion). Following birth, the gestational sac is no longer necessary and is separated from the newborn by severing of the umbilical cord. Following parturition the gestational sac, commonly referred to as the afterbirth, is disposed of as medical waste. However, the tissues of the afterbirth are increasingly being harvested as sources of valued biomedical materials. This is particularly true of the amnion.

The amnion was first used nearly a century ago to treat granulating wounds and burned or ulcerated skin surfaces. More routine use of amnion and chorion began in the 1950's, targeting caustic, chemical and flame burns (Dj 1950, Kirschbaum 1955, Perfil'Ev 1959, Pigeon 1960, Scheibe 1966, Sterling 1956, Zubovich 1963). The value of amnion in medical procedures is highlighted by the proposal to establish an amnion bank in the 1960's (Dino et al. 1966).

Contemporary medicine has witnessed an explosive increase in the utility of amniotic membrane. Vaginal reconstruction (Ashworth et al. 1986, Mhaskar 2005, Morton et al. 1986, Tancer et al. 1979, Zafar et al. 2007), surgical correction of male urethra strictures (Koziak et al. 2004) and treatment of venous leg ulcers (Zubovich 1963) have all employed human amniotic membrane. However, the most prevalent use of amnion in surgical procedures involves the eye (Kaup et al. 2008).

Amniotic membrane transplantation for the treatment of ocular surface disorders has become routine within the past decade. Thermal and chemical burns, pterygium and other disorders of the eye have been treated with amniotic membrane (Park et al. 2008, Sangwan et al. 2007, Srinivas et al. 2007, Tejwani et al. 2007). Ocular surface reconstruction employing amniotic membrane frequently improves patient outcome and reduces associated pain. In many countries, Eye Banks collect and preserve amniotic membrane to address shortages of corneas donated for transplantation.

Recent interest in the amnion and chorion has been heightened by the demonstration of stem cell populations within these tissues (Kim et al. 2007, Kim et al. 2006, Marcus et al. 2008, Marcus et al. 2008, Miki et al. 2007, Miki et al. 2006, Soncini et al. 2007)]. The concept of 'regenerative medicine', repairing or replacing diseased tissue through stem cell therapies, has moved forward to the clinic. Multiple stem cell populations have been identified in the amnion and chorion. Any, or all, may have future clinical utility, potentially playing a role in regenerative medicine approaches.

Irrespective of ultimate use, methodologies and/or devices that facilitate the harvest and, in some cases, storage of amnion and chorion would prove beneficial to the health care community. Contemporary methodologies, using standard medical cutting devices such as scalpels and scissors to generate samples of amnion and chorion are cumbersome. As the demand for these biological materials grows, novel approaches to sample procurement will be needed. The present invention describes a hand-held device that simplifies the harvest of amnion and chorion from the afterbirth. Additional features that facilitate subsequent storage of the isolated biological materials are likewise described.

SUMMARY OF THE INVENTION

The present invention relates to a device and methodology for generating tissue samples from biological materials. More specifically, the present invention relates to a tissue harvesting device that integrates a system facilitating subsequent storage of tissue samples. Even more specifically, the present invention generally relates to a device allowing for the rapid procurement of samples of amniotic membrane ("amnion") and chorionic membrane ("chorion") to facilitate subsequent use or storage of said biological material.

One aspect provides a device for sampling an amniotic membrane or chorionic membrane. The device generally comprises a first arm, a second arm, a cutting element, and a storage vessel. The storage vessel is attached to the first arm or the second arm. The device has an open position and a closed position. A biological material comprising an amniotic membrane or chorionic membrane can be positioned between the first arm and the second arm when the device in an open position. Application of a sufficient force on at least one of the first arm or the second arm closes the device such that a sample of the biological material is cut and deposited into the vessel.

In some embodiments, the storage vessel is detachably attached to the first arm or the second arm. In some embodiments, the cutting element is operably attached to the first arm and the storage vessel is detachably attached to the first arm. In some embodiments, the cutting element is operably attached to the first arm and the storage vessel is detachably attached to the second arm. In some embodiments, the cutting element and the storage vessel are substantially aligned when the device is in the closed position.

In various embodiments, the storage vessel is a sealable storage vessel and application of a sufficient force on at least one of the first arm or the second arm closes the device such that a sample of the biological material is cut and deposited into the vessel and the storage vessel is sealed.

In various embodiments, the storage vessel of the device comprises a cap and a vial. In some embodiments, the vial comprises the cutting element. In some embodiments, the cap comprises the cutting element.

In various embodiments, the vial comprises a seal and the seal of the vial is breached when the device is moved to the closed position. In some embodiments, the vial contains a biological medium and the seal of the vial retains the biological medium within the vial.

In various embodiments, the device comprises a detachably attached cassette. The cassette has various configurations, including (i) at least one storage vessel; (ii) a plurality of storage vessels; (iii) at least one cutting element; (iv) a plurality of cutting elements; (v) at least one storage vessel and at least one cutting element; (vi) a plurality of storage vessels and at least one cutting element; and (vii) a plurality of storage vessels and a plurality of cutting elements.

In some embodiments, the cassette comprises a plurality of storage vessels and a corresponding plurality of cutting elements; and closing the device results in cutting of the sample of the biological material, deposition of the sample in the storage vessel, and advancement of the cassette to a next storage vessel. In some embodiments, the cassette comprises a linear array of storage vessels or a circular or semicircular array of storage vessels.

In some embodiments, the cassette comprises one or more cutting elements and at least a portion of one or more storage vessels. In some embodiments, the storage vessel comprises a cap and a vial and the cassette comprises either or both of the cap and the vial.

In some embodiments, the device comprises a plurality of cutting elements and a corresponding plurality of storage vessels, wherein closing the device results in cutting of a plurality of samples of the biological material by the corresponding plurality of cutting elements, and deposition of the plurality of samples in the corresponding plurality of storage vessels.

In various embodiments, the storage vessel comprises a tracking device selected from the group consisting of a barcode or a radio frequency identification tag.

Another aspect provides a method of sampling an amniotic membrane or chorionic membrane. The method includes positioning a biological material comprising am amniotic membrane or chorionic membrane between the first arm and the second arm of any of the various devices as described above in an open position; and closing the device such that a sample of the biological material is cut and deposited into the vessel.

In various embodiments, the method includes inserting a cassette comprising a plurality of storage vessels, as described above; closing the device such that a sample of the biological material is cut and deposited into at least one of the vessels; and advancing the cassette to align an unused vessel. In some embodiments, the cassette comprises a plurality of storage vessels and a corresponding plurality of cutting elements, and opening the device results in advancement of a storage vessel.

Another aspect provides a kit for collecting and storing a sample of an amniotic membrane or chorionic membrane. In some embodiments, the kit can include a device as described above. In some embodiments, the kit can include a cassette as described above. In some embodiments, the kit can include one or more of instructions, reagents, storage media, cutting elements, storage vessels, tracking devices, labels, or cleaning supplies.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 5. Top and front view of one embodiment of the device.

FIG. 6. Side view of cap/cutting element, cryovial and sealed vial containing biological sample.

FIG. 8. Top view of cassettes containing cryovials designed to integrate with the device.

DETAILED DESCRIPTION OF THE INVENTION

The present invention relates to a device and methodology for generating tissue samples from biological materials. More specifically, the present invention relates to a tissue harvesting device that integrates a system facilitating subsequent storage of tissue samples. Even more specifically, various embodiments of the device of the present invention allow for the rapid procurement of samples of amniotic membrane ("amnion") and chorionic membrane ("chorion") to facilitate subsequent use or storage of said biological material.

One aspect of the invention is a device comprising a cutting element (3). The device can include an apparatus to position the cutting element in proximity to a biological material. The device can further include a mechanism for removal of a sample from the biological material. The device can further include a sample collection module (4) that allows collection of the sample of biological material.

Figure 1:
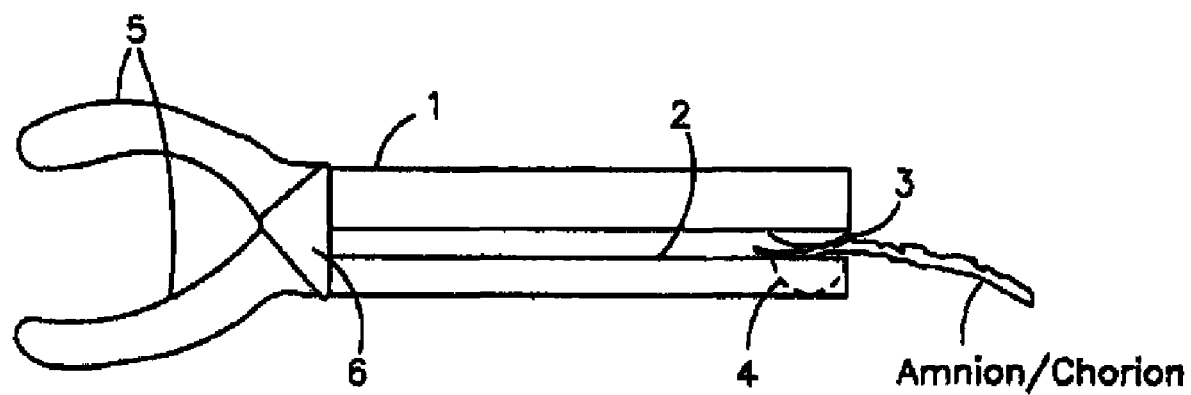
FIG. 1. Side view of one embodiment of the device. Biological samples (amnion/chorion) are interposed between moveable arms containing the cutting element (top arm) and the sample receptacle (bottom arm). Forces applied to the handles act through the hinge (pivot point) and bring the cutting element into contact with the biological material. Cut material is retained within a hollow area (sample receptacle) incorporated within the lower arm of the device (dotted line).

The device of the present invention can comprise paired moveable arms (1, 2). At least one arm can contain a cutting element. The first arm (1) can be operably connected to a base or a second arm (2), or a combination thereof. A first arm (1) can interact with a base or a second arm (2) across a pivot point (6) to bring the cutting element (3) into close apposition with the biological material, allowing cutting of a sample from the biological material (see e.g., FIG. 1).

The device can be hand-held. In some embodiments the device resembles pliers (see e.g., FIG. 1). Application of a force on one side of the pivot (6) can cause closure of the arms (1, 2) on the opposing side of the pivot (6), which can bring the cutting element (3) in contact with the biological material of interest. In addition to cutting the biological sample, the applied force can facilitate deposition of a cut sample into a receptacle (4).

Figure 3:
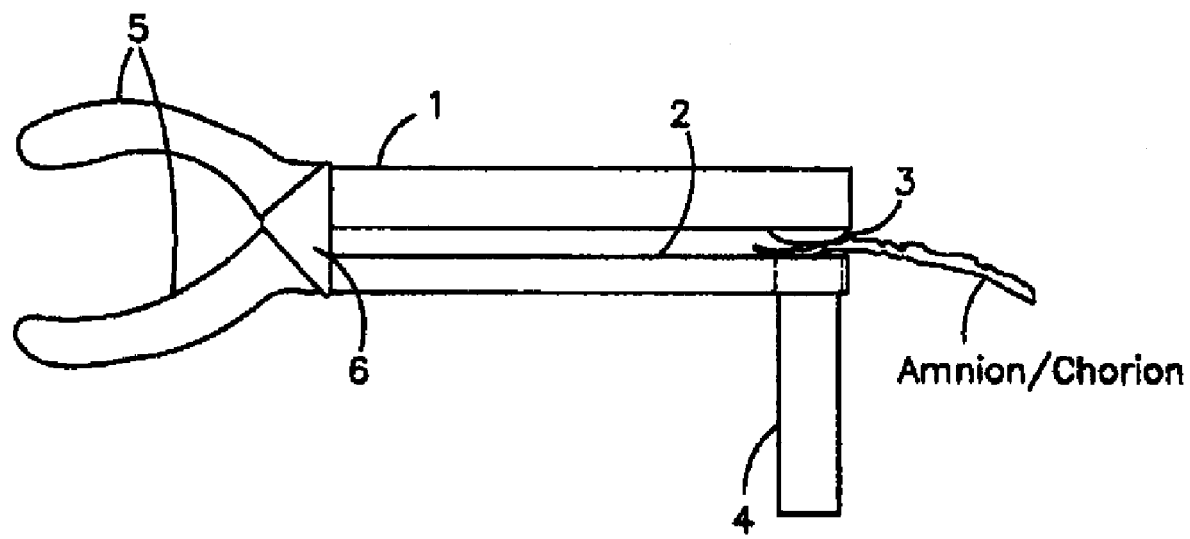
FIG. 3. Side view of one embodiment of the device. Biological samples (amnion/chorion are interposed between moveable arms containing the cutting element (top arm) and the sample receptacle (bottom arm). Forces applied to the handles act through the hinge (pivot point) and bring the cutting element into contact with the biological material. Cut material passes through a void in the lower arm of the device (dotted line) and is retained within a removable sample-receiving vial.

In some embodiments, the device comprises paired moveable arms in which a first arm (1) contains a cutting element (3) and a second arm (2) contains a receptacle (4) to receive the generated biological sample (see e.g., FIG. 3). A hinged area (6) can serve to align the first (1) and second arms (2) and provide a pivot point (6) across which application of force can bring the arms into close proximity and allows cutting of the biological material.

The device can be comprised of any suitable material known in the art. Preferably, the device comprises a cleanable material, and more preferably, the device comprises a material suitable for subsequent sterilization by autoclave, irradiation or other appropriate methodologies.

The device can be a single use or a multiple use device. In some embodiments, the device is reusable device. In some embodiments, the device can be engineered to be a single use, disposable item. Preferably, a disposable device is constructed of materials and built to specifications that encourage single use. For example, a device, or a portion thereof, can be produced with an inexpensive thermoplastic, preferably formed according to the process of injection molding. The device can comprise, for example, polyvinyl chloride, polyethylene, polypropylene, or other similar materials. As another example, the device, or a portion thereof, can comprise a metal or metal alloy.

In one embodiment the cutting element (3) is a sharpened cutting edge (blade) that can shear a biological material when a force is applied. The cutting element (3) can comprise a serrated edge, a straight edge, or a combination thereof. Preferably, the cutting element (3) substantially or completely circumscribes a sample, removing it from the biological material and depositing the sample in a receptacle (4), preferably a receptacle incorporated into the device.

In some embodiments, the cutting element (3) of the device can be derived from the same material as the cap (8) of the device, allowing manufacture in a single process. In some embodiments, the cutting element (3) of the device can be derived from a different material as the cap (8) of the device. For example, the cutting element (3) can be a metal or metal alloy whereas some or all of the remaining components can be a plastic and molded around the cutter through an injection molding process.

In some embodiments, the cutting element (3) comprises a metal that can be heated by, for example, electrical resistance. The heated cutting element (3) can remove a sample from a biological material by burning through the circumscribed tissue. As described above, the sample can be deposited and retained within the incorporated receptacle (4). Such an embodiment would require a power source, preferably incorporated into the device in the form of, for example, a battery. Alternatively, the device could be powered via connection to an electrical outlet.

The cutting element (3) can remove a sample of a variable or fixed size. Preferably, a cutting element removes a sample of a single, defined size. Various embodiments of the device can be used to generate biological samples of appropriate dimension for applications including, but not limited to, biological dressings, ocular resurfacing, stem cell isolation, or other biomedical interventions.

A cutting element (3) and a sample receptacle (4) can be interchangeable units that attach to a base or arm (1, 2) of the device. For example, a single base device, comprising handles (5), a hinge (6), and moveable arms (1, 2) can accept cutting elements (3) of varied size, allowing said base device to alternatively be used for isolation of samples intended for various procedures, such as biological dressing, ocular resurfacing, stem cell isolation, or other biomedical interventions.

Figure 2:
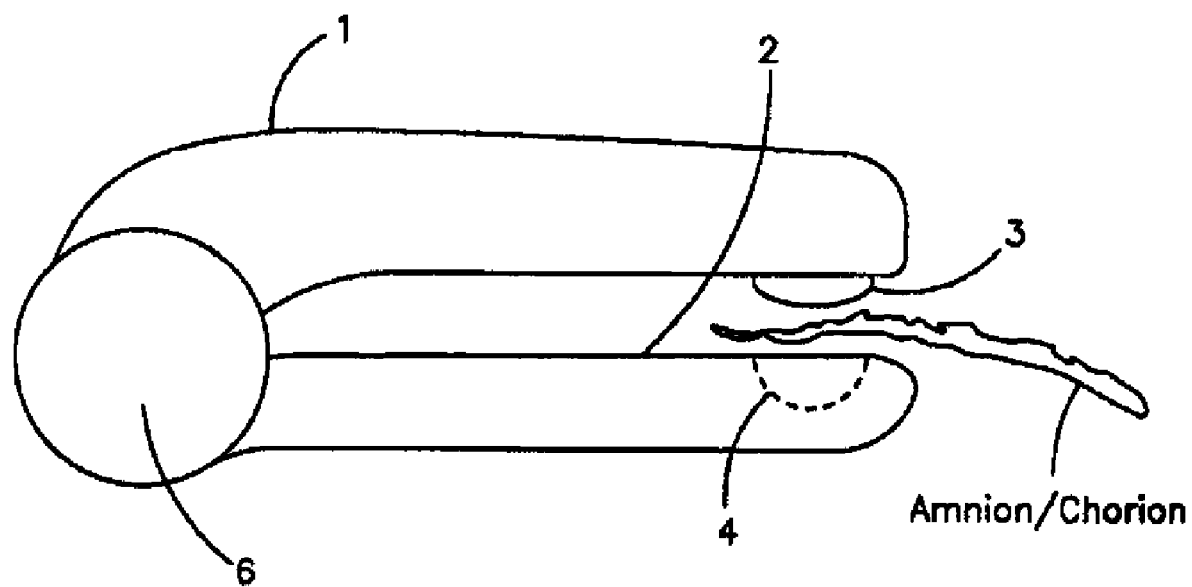
FIG. 2. Side view of alternate embodiment of the device. Moveable arms containing a cutting element (top arm) and a sample receptacle (bottom arm) are joined by a hinge at one end. Forces applied simultaneously to top and bottom arms brings cutting element in contact with the biological material (amnion/chorion), removing a sample of defined size. The cut sample is retained in the hollow sample receptacle incorporated within the lower arm of the device (dotted line).

In one embodiment, the device resembles an office stapler, in which all moving parts are on one side of the pivot (6) (see e.g., FIG. 2). The pivot (6) can maintain alignment of the moveable arms (1, 2) and can allow a force applied to the arms of the device to bring said arms into close apposition. Samples of reproducible size can be cut from biological materials interposed between the arms (1, 2) of the device. Cut samples can be retained within the receptacle (4) as described above. All versions and characteristics described above can apply equally to this embodiment of the device.

In some embodiments, the device generates samples of a fixed size. In some embodiments, the device accepts interchangeable cutting elements (3) for biological samples of varied sizes.

Size of the cutting element (3) can be according to desired application of the biological sample. For example, amnion samples for ocular reconstruction are preferably from about 1.5 cm×about 1.0 cm up to about 3.5 cm×about 3.5 cm in size.

Smaller or larger sample sizes could be accommodated, as determined by need. As another example, amnion samples for stem cell storage are preferably circular tissue samples of about 0.5 to about 0.9 cm diameter. As another example, amnion samples for biological dressings are comparatively large and can be trimmed to size within a clinical setting. Exemplary sample size for biological dressings include about 10 cm×about 10 cm to about 20 cm×about 20 cm.

Figure 4:
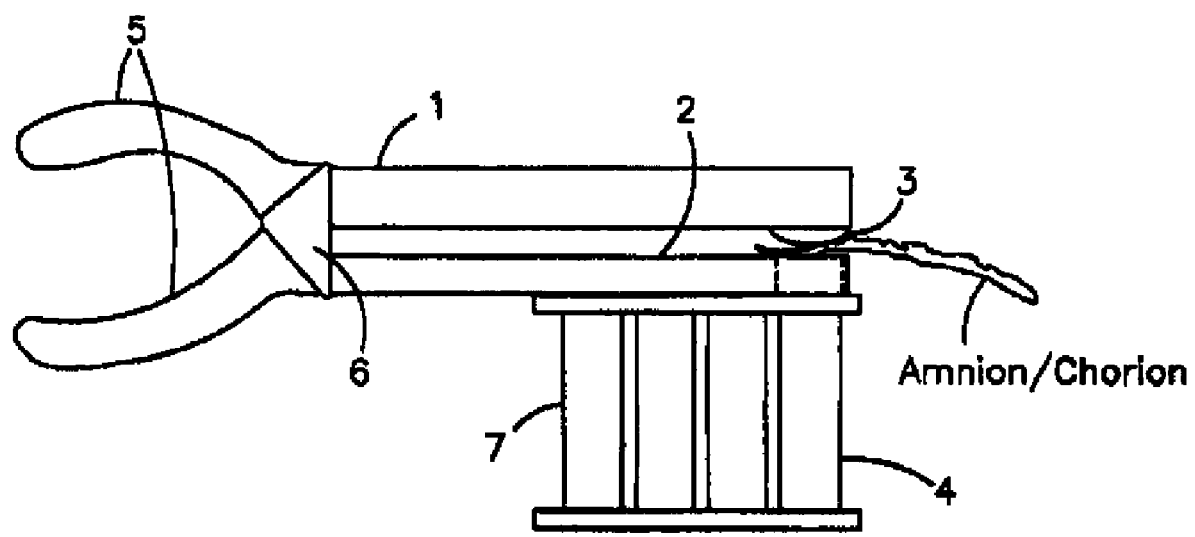
FIG. 4. Side view of one embodiment of the device. Biological samples (amnion/chorion are interposed between moveable arms containing the cutting element (top arm) and the sample receptacle (bottom arm). Forces applied to the handles act through the hinge (pivot point) and bring the cutting element into contact with the biological material. Cut material passes through a void in the lower arm of the device (dotted line) and is retained within a sample receiving vial residing within a cassette that contains multiple vials. Cassette position can be changed independent of the cutting device, positioning an alternate vial for sample receipt.
Figure 4A:
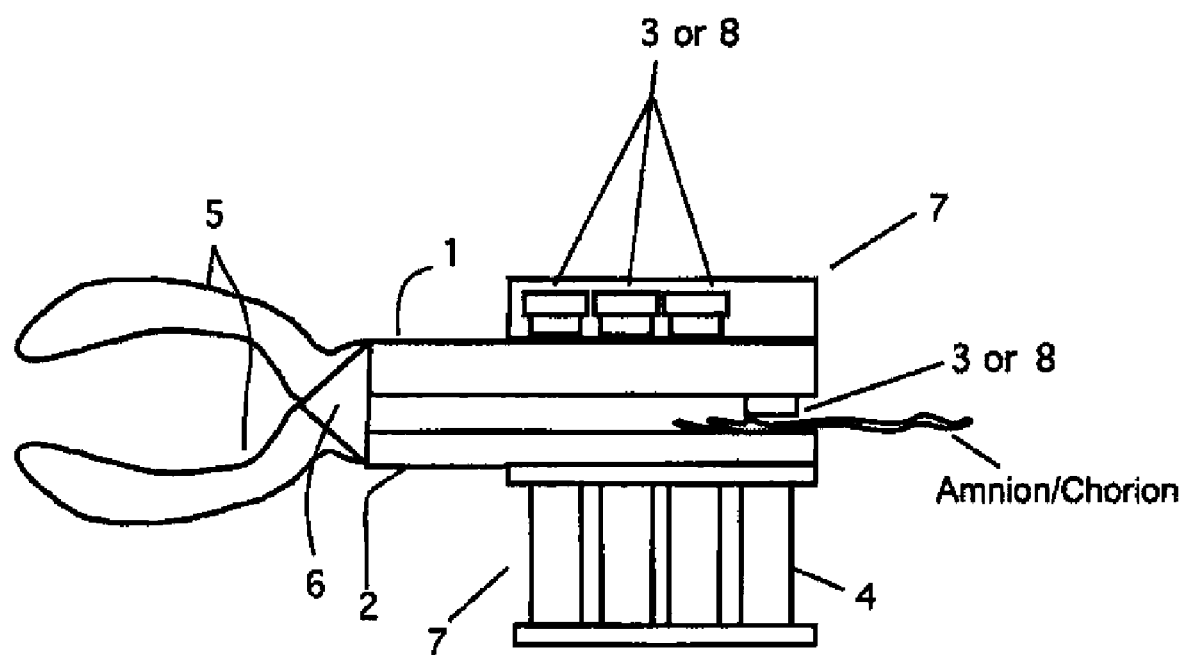
FIG. 4A illustrates a first cassette connected to a first arm of the device and a second cassette connected to a second arm of the device.
Figure 5A:
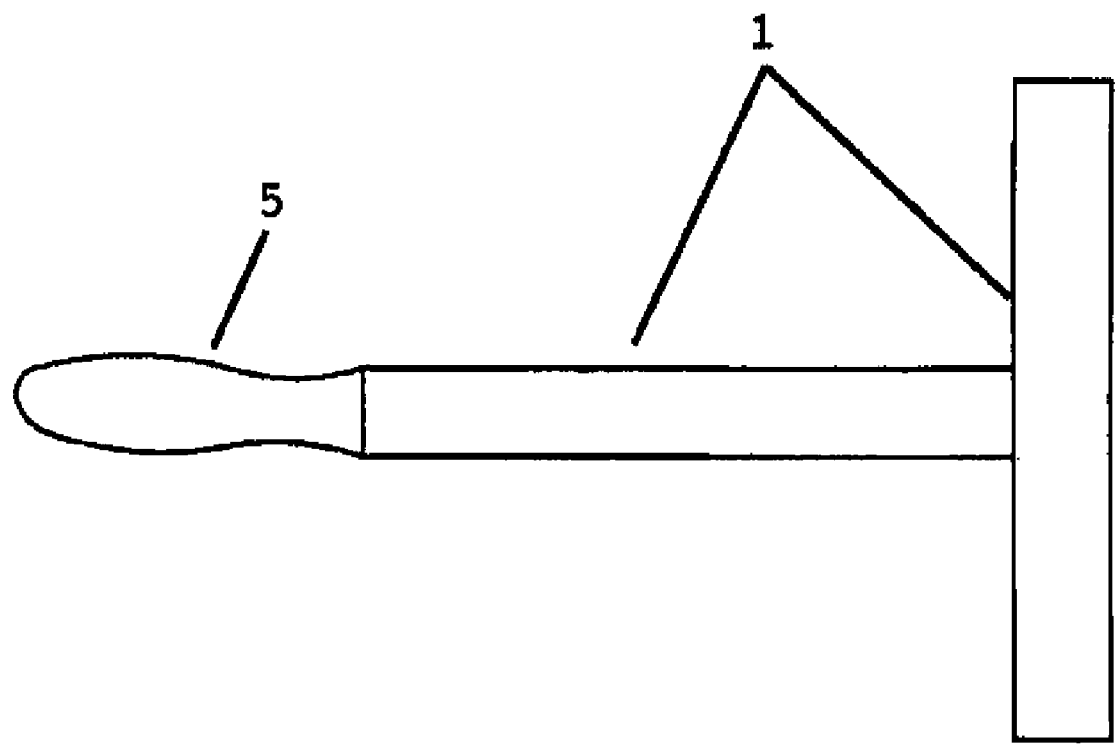
In FIG. 5A, the top view demonstrates position of perpendicular appendages containing cutting elements and sample receptacles.
Figure 5B:
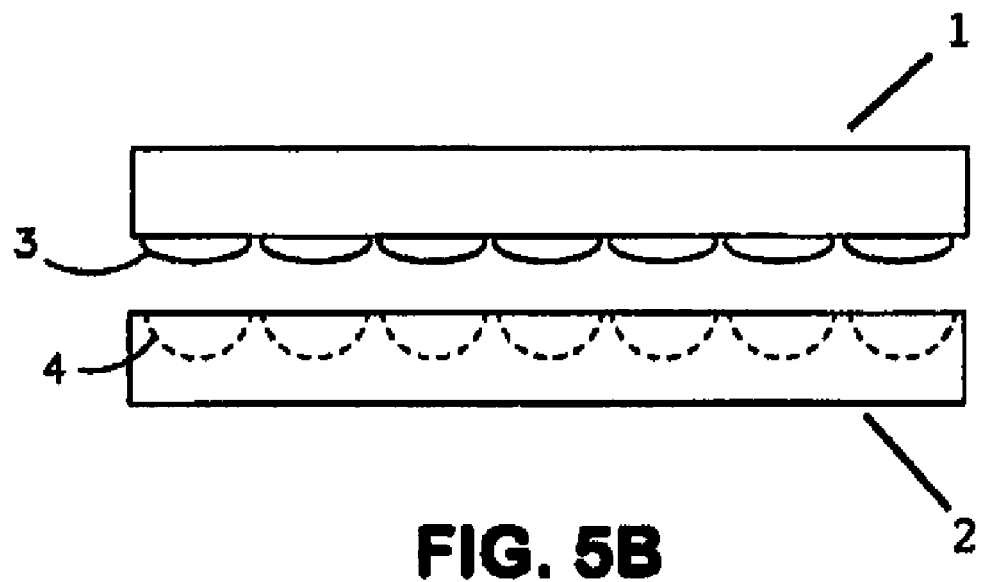
In FIG. 5B, the front view shows face-on view of perpendicular appendage containing arrayed cutting elements and mated sample receptacles. Biological samples (amnion/chorion) are interposed between moveable arms containing the cutting elements (top arm) and the sample receptacles (bottom arm). Forces applied to the handles bring the cutting elements into contact with the biological material. Cut materials are retained within the arrayed sample receptacles.

Another aspect allows for generation of multiple samples simultaneously. The device can employ an additional perpendicular appendage at the end of the moveable arm (1 or 2) furthest removed from the pivot (6) (see e.g., FIG. 5). The perpendicular appendage can contain an array of cutting elements (3) that simultaneously cut multiple samples when a force is applied that results in the moveable arms (1, 2) being brought into close apposition. Each individual cutting element (3) can be mated with a receptacle (4) to receive the sample of cut biological material. In the preferred embodiment, a storage vessel(s) (4) is/are incorporated into the device (see e.g., FIG. 4) to receive samples and facilitate subsequent transport and/or storage.

Various aspects allows for the deposition of samples generated by the above device(s) directly into vessels (4) designed for storage (see e.g., FIG. 3). In one embodiment the vessels are cryogenic vials (e.g. Corning Product #430289). In one aspect the cryogenic tubes are pre-filled with a sterile liquid medium to maintain cell viability during transport and/or storage. In one incarnation the liquid media is a commercially available transport media developed to maintain cell viability. An example is HYPOTHERMOSOL® FRS (HTS-FRS) manufactured by Biolife Solutions. Alternatively, standard growth medias routinely used in the biomedical field, including Dulbecco's modified Eagle's media (DMEM), AMNIOMAX® (Invitrogen) or any other comparable growth medias could be employed. Media may be supplemented with additional growth factors, serum components, antibiotics, or any other factors that enhance the survival or facilitate subsequent processing of the biological sample.

The cryovials (4) would most appropriately be molded from polypropylene. In one embodiment commercially available cryovials would be employed.

In one embodiment the cryogenic tubes (4) are pre-filled with cryogenic medium allowing for subsequent storage of said biological materials at a temperature below about −80° C. Cryogenic media may include commercially available solutions (e.g. CRYOSTOR™ Biolife Solutions) or any other solution that enhances the survival of cells and tissues stored below about −80° C.

In circumstances where the viability of cells contained within the biological sample is unnecessary or detrimental, solutions that compromise the viability of the resident cells within the sample can be employed.

The open end of the pre-filled tubes (4) can be sealed with a penetrable foil or plastic seal (12) that maintains sterility of the contents. The vial seal (12) can be removed prior to generation and deposition of the biological sample. Preferably, the cutting element (3) punctures the seal (12) concomitant with the generation of the biological sample, allowing sample isolation and deposition of said sample in the receptive vial (4) in response to an applied force to the device. More preferably, the cutting element (3) is incorporated into a cap (8) mated to the receptive vial (see e.g., FIG. 6). The device can simultaneously cut the biological sample, deposit said sample in the receptive vial (4), and cap (8) the vial, all in response to an applied force. Accomplishment of the above can be according to repeated (i.e., more than one) application of force to the device.

A vessel (4) can be pre-filled with a preservation media, such as a cryopreservation media. Vessels (4) released from a device can be slowly cooled to about −196° C., or another temperature suitable for cryopreservation, using a controlled rate freezer. Samples can then be moved to liquid nitrogen for longer term storage. Sample integrity an be determined by checking cell viability using techniques known to the art.

The device can sample biological materials of human origin, or non-human origin. Preferably, sampled materials are of non-human mammalian origin, more preferably of human origin.

The amnion and chorion can be physically separated by peeling the two membranes apart. Samples of amnion and/or chorion can then be generated using the device. Samples of amnion and chorion can be generated simultaneously by cutting juxtaposed, non-separated membranes.

Figure 8A:
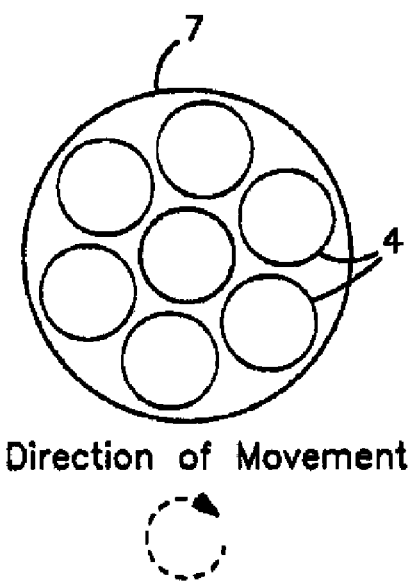
In FIG. 8A, the turret design contains liquid filled, foil-sealed cryovials arranged in a circular fashion. One cryovial is aligned with the cutting element. Forces applied to the device harvest the biological sample and cap the vial. Torque applied to the cassette moves the capped vial out of the receiving position and positions an unused vial beneath the cutting element. The process is repeated until all vials have been used. element. The process is repeated until all vials have been used.
Figure 8B:
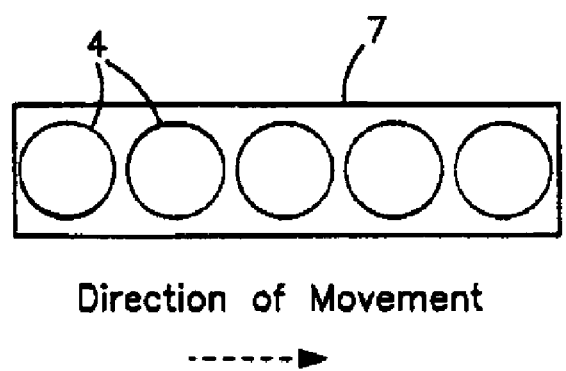
In FIG. 8B, the linear design contains liquid filled, foil-sealed cryovials arranged in a linear fashion. Interaction of vials with cutting element are as described above. Forces along the long axis of the cassette advance cryovials to the receiving position.

A device of the present invention can comprise a cassette (7). A cassette (7) can comprise one or more of a sample receiving vessel (4), a vessel cap (8), or a cutting element (3). A device can be configured to accept a cassette (7) containing multiple sample receiving vessels (4) (see e.g., FIG. 4). The cassette (7) can hold a plurality of sample vessels (4) in a linear fashion (see e.g., FIG. 8B). Alternatively, a cassette (7) can resemble a turret, with sample vials (4) arranged in a circle or a semi-circle (see e.g., FIG. 8A).

A cassette (7) can be formed of any suitable material. Preferably, a cassette (7) is formed of the same or similar material as other components of the device. For example, a cassette (7) can be formed by injection molding from the same or similar plastic as a body of the device.

Advancement of a cassette (7) can occur subsequent to collection of a biological sample. Advancement of the cassette (7) can be manual or automated. In some embodiments, an applied force to the device cuts a biological material and deposits a sample thereof within a receiving vessel (4) and subsequently advances the cassette (7), thereby aligning a different sample vessel (4) with the cutting element (3). In some embodiments, a cassette (7) is advanced by other means, including, but not limited to, direct application of force to the cassette (7) by the operator. Preferably, a single applied force to the device cuts the biological material, deposits it within the receiving vessel (4), caps (8) said vessel, and advances the cassette (7).

A device of the present invention can employ multiple cutting elements (3) and mated sample receptacles (4). In some embodiments, the device provides for simultaneous collection of multiple biological samples. A substantially perpendicular appendage containing a plurality of cutting elements (3) and receptacles (4) can be secured to moveable arms (1, 2) (see e.g., FIG. 5A). Biological material to be sampled can be interposed between the appendages (1, 2), juxtaposed to the cutting elements (3) (see e.g., FIG. 5B). Application of a force to the device can result in the simultaneous generation of multiple samples, which can be collected in one or more receptacles (4), preferably in a single receptacle (4) corresponding to a single cutting element (3). Multiple cutting elements (3) and receptacles (4) can be aligned along the moving arm (1 or 2) of the device, reducing or eliminating the need for a perpendicular appendage.

A sample vessel contained within a removable cassette (7) can collect generated biological samples. Alternatively, a cutting element (3) is contained within a vessel cap (8), allowing for sample generation and vessel sealing as a result of an applied force. All variations described above for devices generating single samples apply equally to these embodiments.

Figure 6A:
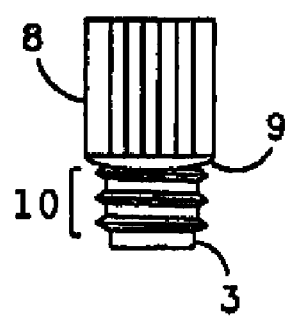
In FIG. 6A, the cap/cutting element consists of an external portion, a sealing O-ring, a threaded region that interlocks with the cryovial and a cutting element to harvest the biological material.
Figure 6B:
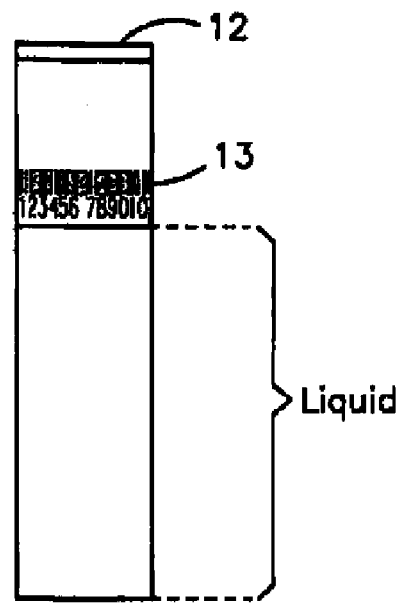
In FIG. 6B, the vial is pre-filled with liquid and an airtight seal formed with a foil seal. An identifier is integrated within the cryovial for sample identification and tracking. The nature of the liquid contained within the vial is determined by intended end use of the biological sample.
Figure 6C:
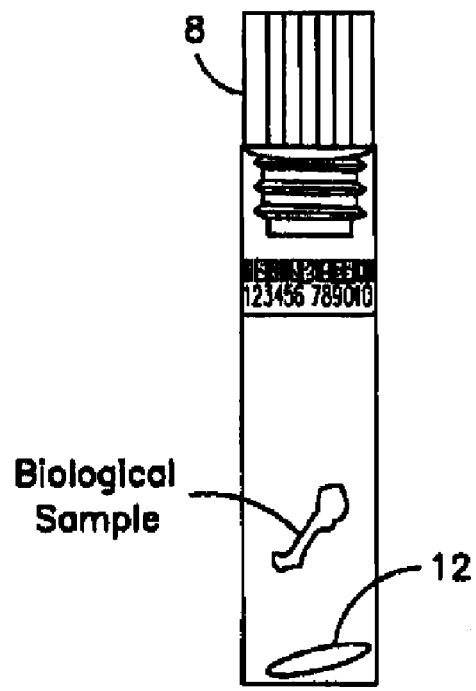
FIG. 6C shows the side view of the integrated cap/cutting element and cryovial after harvesting of biological material. After cutting the sample and foil seal are released into the cryovial and the cap forms an airtight seal with the cryovial.

In some embodiments, for example those designed for cryopreservation of biological samples, a vessel cap (8) can comprise an embedded cutting element (3) and a mated, foil-sealed (12) vessel (4) (see e.g., FIG. 6). The cap (8) can include one or more of an external portion, an O-ring (9) or gasket, a threaded region (10), and a cutting element (3). Preferably, the vessel (4) is constructed of a material, generally plastic, that is able to withstand large changes in temperature (e.g., from about +121° C. to about −196° C.) and humidity (e.g., ranging from 0% to 100%). An exemplary vessel (4) has an inside diameter of about 1 cm and a volume of about 1.0 to about 5.0 ml. Smaller or larger vials (4) can also be utilized. Preferably, the vessel (4) is sealed at one end with a thin foil or plastic material (12). In some embodiments, the vessel is pre-filled with a sterile liquid medium.

Figures 7A, 7B, 7C, 7D:
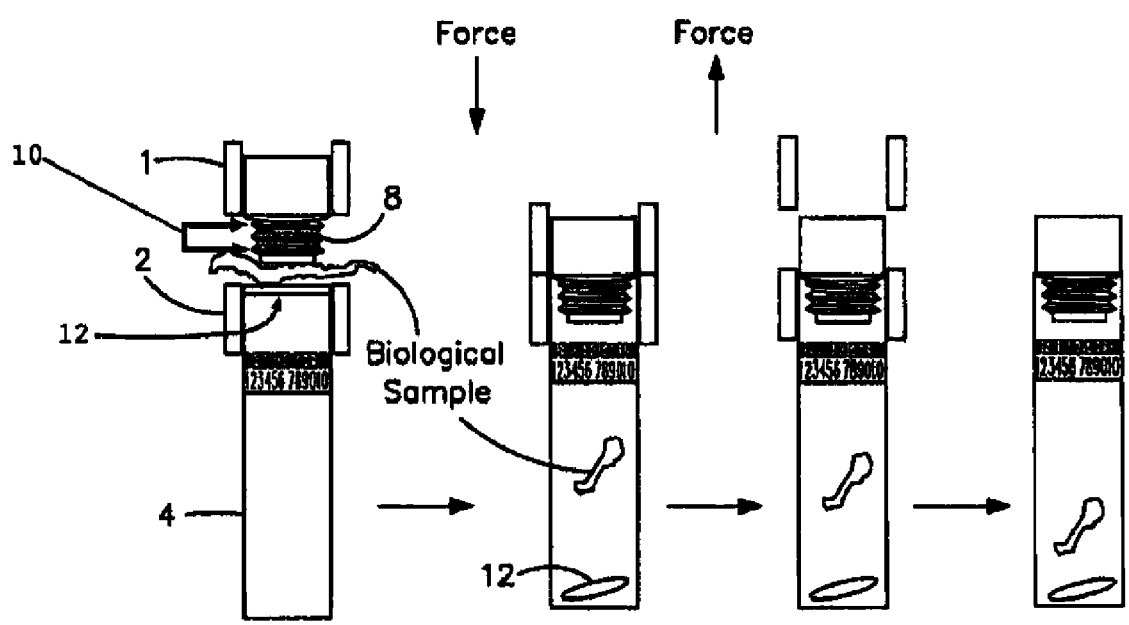
FIG. 7. Detailed view of device in use. a. Device contains the cap/cutting element in the upper moveable arm and the foil-sealed cryovial present in the lower arm. The biological material to be sampled is interposed between the cutting element and the foil. force is then applied to bring the cutting element in contact with the biological material. b. Applied force cuts the biological material and the foil seal, which drop into the cryovial. Continued application of force presses the cap into the cryovial, Forward movement of the cap is stopped by contact of the O-ring with the cryovial, forming an airtight seal. Integral components within the device apply force in the direction opposite to the initial applied force. c. The cap remains integrated within the cryovial and is released. d. The sealed cryovial containing the biological sample is released from the device.

A biological material to be sampled can be interposed between a cap (8) and a sealed (12) vessel (4) (see e.g., FIG. 7). Preferably, one or more of a cap (8), cutting element (3), or vessel (4) are loaded into a device. A force exerted on the cap (8), vessel (4), or both can result in contact between the cutting element (3) and the biological material and a cutting of a sample core from the biological material. The cutting element (3) can subsequently contact a foil seal (12) of the vessel (4), piercing this material. The biological sample, and optionally the foil seal (12), can drop into the vessel (4) and be retained. A continued application of force, or a new force, can insert the cap (8) into the throat of the vessel (4). Movement of the cap (8) into the vessel (4) can be ultimately impeded by friction fit of the cap (8) and vessel (4) through, for example an O-ring (9) on the cap (8) or in the neck of the vessel (4), thereby forming a seal. Threads of the cap (8) can interact with mated internal threads of the vial (4), securing the cap (8) to the cryovial (4). The threads (10) on the cap (8) can be recessed and interact with external threads on the vessel (4). The threads of the cryovial (4) can be replaced by a leur lock system, which similarly ensures retention of the cap (8) or cutting element (3) within the cryovial (4). Any other system that retains the cap (8) within the vessel (4) and maintains a sufficiently tight seal between the vessel (4) and the cap (8) are applicable. The sealed cryovial (4) containing the biological sample can be released and transported or stored. In some embodiments, the forces necessary and sufficient to perform some or all of the actions described herein can be imparted manually.

A cutting element (3) can be contained within the vial (4). The cutting element (3) can contact and cut a foil seal (12), subsequently contacting and cutting a sample from a biological material. Sealing of the vessel (4) by the cap (8) and retention of the biological sample within the cryovial (4) can be in accord with the description above.

Multiple vessels (4) can be contained within a cassette (7), allowing for generation of multiple samples for storage. For example, a plurality of more than one vial (4) can be arranged in series. Arrangement of vessels (4) within the cassette (7) can be linear (see e.g., FIG. 8B) or circular or semi-circular (see e.g., FIG. 8A). The cassette (7) can be inserted into a receptacle of the device such that a foil sealed (12) vessel (4) of the cassette (7) is aligned directly under a cutting element (3). A force applied to the device can result in generation of a biological sample, retention of said sample within the vessel (4), and sealing of the vessel (4) with the cap (8). Torque applied to the cassette (7) can move the sealed vessel (4) out of its position and align the next vessel (4) in the series in position to receive a sample. An unused cap (8) or cutting element (3) can be put in position above an unused vessel (4) (e.g., a sealed vial) and the process of tissue sample procurement repeated. Alternatively, a plurality of vessels (4) can be arranged in a linear cassette (7). The cassette (7) can be inserted into the device as described, either parallel, perpendicular, or at an acute angle relative to a moveable arm (1, 2) of the device. Alignment of a foil sealed (12) vessel (4) with a cutting element (3), generation of a sample, and insertion of the cap (8) into the vial (4) can occur as described above. A force applied along an axis of the cassette (7) can move the sample-containing vessel (4) out of the receiving position and align the next vessel (4) in series into the receiving position.

The force necessary to move a used (i.e., sample containing, sealed) vessel (4) out of the receiving position and to position an unused vessel (4) in the receiving position can be generated by a mechanical action inherent to operation of the device. Alternatively, a user can manually apply a force to advance the cassette (7).

The cap (8) or cutting element (3) can be contained within a cassette (7) mounted above the device that moves in concert with a vessel (4)-containing cassette (7) mounted below. A force that positions a cassette (7) into the receiving position can simultaneously load a cap (5) or cutting element (3) in position to perform the cutting and sealing steps.

The device can contain an integrated component that returns the moveable arms (1, 2) to the open position.

Of course, a cap (8) and a cutting element (3) can be individual units not part of a cassette (7). Further, samples can be generated by a cutting element (3) that is not incorporated into the cap (8). Sample cassettes (7) can be advanced as described and individual vessels (4) capped (8) in a second step not directly coupled to sample isolation.

The cassette (7) can be configured to deliver to the vessel (4) an associated barcode or RFID (13) to facilitate sample identification and tracking, as described further below.

The device of the present invention can comprise a tracking system (13). Monitoring or tracking for storage or distribution of vessels containing a biological sample collected from a device described herein can be according to numerous solutions know in the art.

In some embodiments, a sample vessel (4) (e.g., a cryogenic vial) can incorporate a barcode (13) for sample identification and tracking. A barcode (13) can be incorporated in a label affixed to the vessel (4). A barcode (13) can be incorporated directly into or onto the vial (4) using laser etching or other appropriate methodologies. A barcode (13) an be contained on a material (e.g., a disc) within a vessel (4) that could be recovered concomitant with retrieval of the biological sample. The barcode (13) can be integrated within the foil seal (12) of a vessel (4), which can be released by a cutting element (3) and retained along with the biological sample within the vessel (4). A vessel (4) can comprise one or more barcodes (13) in any placement suitable for scanning of the vessel (4). Preferably the barcode (13) can remain intact and readable despite extreme fluctuations in temperature [e.g. about 37° C. to about −196° C.], humidity, or other environmental conditions.

Some embodiments can employ a radio-frequency identification (RFID) system (13). A RFID tag (e.g., a passive RFID tag) (13) can be incorporated into a vessel (4), for example in the base of a cryovial. Energy supplied by a reader (e.g., a low-level radio frequency magnetic field) can activate RFID tag (13) and allow for the transmission and reception of sample information. A RFID tag (13) can be incorporated within a cap (8) of a vessel (4). A force applied to the device that inserts the cap (8) into a vessel (4) can serve to secure the RFID tag (13), facilitating identification of the biological sample contained therein. A RFID tag (13) can be incorporated into a disc which can reside within the cavity of the vessel (4) prior to harvesting of the biological sample and application of the cap (8). A RFID tag (13) can be integrated within a foil seal (12) of a vessel. The RFID tag (13) can be released by a cutting element (3) and retained within the vessel (4) along with the harvested biological sample.

Use of any of these tracking methods, or other know in the art, for sample identification are not mutually exclusive. For example, barcodes (13) incorporated into a cryovial (4), internal discs, foil seal (12), or any other applicable location can be used in any combination of two or more. Similarly, RFID tags (13) incorporated into the cryovial (4), existing on an internal disc, contained within the foil seal (12), incorporated into the cap (8), or any other feasible location could be employed in any combination of two or more. Likewise, a barcode and an RFID tag (13) can be used in any combination of two or more.

Another aspect of the invention is directed towards a kit that can allow for easy sample isolation and can facilitate subsequent transport and/or storage of isolated tissues. Such kits can include some or all components of the device of the present invention and, in certain embodiments, instructions for use.

Various components of the kit can be packaged in one or more containers. In some embodiments, a device and a cassette (7) containing one or more pre-filled vials (4) can be separately packaged. In other embodiments, the device and a cassette (7) of cryovials (4) can be packaged within the kit fully assembled and ready for use. For example, contained within an outer packaging of the kit are individual components that, once assembled, allow for sample procurement and transport/storage of same. Preferably, at least the components of the kit that contact a biological surface are sterile. More preferably, all components of the kit are sterile and the outer container air tight. Such kits can also contain sanitizing materials that can cleanse or disinfect a biological material or surface (as necessary) prior to sample procurement, or clean a cassette (7) following sample procurement. For example, a kit can contain one or more individually packaged single-use alcohol cleansing pads (e.g., 70% isopropanol in water). Various embodiments of the kit can facilitate performance of the methods described herein. When supplied as a kit, the different components of the device can be packaged in separate containers and assembled immediately before use. Packaging of the components separately can, if desired, be presented in a pack or dispenser device which may contain one or more units. The pack may, for example, comprise metal or plastic foil such as a blister pack.

Kits may also include reagents in separate containers such as, for example, sterile water or saline to be added to a lyophilized cryogenic medium packaged separately. For example, sealed glass ampules may contain lyophilized agent (s) and in a separate ampule, sterile water or sterile saline, each of which has been packaged under a neutral non-reacting gas, such as nitrogen. Sample vessels (4) can comprise any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Fluid containers can have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. For example, written instructions can be provided to guide the end user in assembly and usage of a fully-functional device. Assembly of the device, sanitization of the biological material, procurement of samples, removal of a cassette (7), and storage of samples can be instructed in accord with methods described above. For example, written instructions can be provided to guide the end user in assembly and usage of a fully-functional device. In some embodiments, the instruction recite steps necessary and sufficient to insert a cassette (7) into an appropriate receptacle within the device. In some embodiments, the instruction recite steps necessary and sufficient for the end user to obtain multiple biological samples by operating the device one or more times. In some embodiments, the instruction recite steps necessary and sufficient for the cryovials (4) containing samples, remaining within the cassette (7), to be removed conjointly from the device and further processed as determined by need.

In one embodiment, instructions can recite one or more the following steps: instructions provided for kit use would be printed on the outer packaging and read as follows: open outer packaging in clinical setting, taking precautions to maintain sterility; locate the device and insert cassette (7) under lower arm until cassette (7) clicks into place; inspect the biological material to be sampled and locate an intact area of sufficient size to accommodate sample procurement (typically an area of 50-100 cm$^2$); clean both sides of the area with the provided isopropanol wipe; manipulate the biological sample so that it is interposed between the two moveable arms (1, 2) of the device; apply force to the device to cut the biological material, deliver the material to the vial (4) and seal the vial (4); release pressure from the device and allow advancement of the cassette (7); repeat until the cassette (7) no longer advances, signaling that all vials (4) have been used; retract the device from the biological material and remove the cassette (7); wipe down the outside of the cassette (7) with the second isopropanol wipe and process as desired; discard all other materials, including the device, in medical waste.

Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

REFERENCES

Ashworth M F, Morton K E, Dewhurst J, Lilford R J, Bates R G 1986 Vaginoplasty using amnion. Obstet Gynecol 67:443-6
Dino B R, Eufemio G G, De Villa M S 1966 Human amnion: the establishment of an amnion bank and its practical applications in surgery. J Philipp Med Assoc 42:357-66
Dj P-B 1950 [Use of amniotic membrane in caustic and corrosive burns.]. Srp Arh Celok Lek 48:746-8
Kaup M, Redbrake C, Plange N, Arend K O, Remky A 2008 Amniotic membrane transplantation in severe ocular surface disorders. Eur J Opthalmol 18:691-4
Kim J, Kang H M, Kim H, Kim M R, Kwon H C, Gye M C, Kang S G, Yang H S, You J 2007 Ex vivo characteristics of human amniotic membrane-derived stem cells. Cloning Stem Cells 9:581-94
Kim S J, Yoo J H, Kim B S, Oh J H, Song C H, Shin H J, Kim S H, Choi C W, Kim J S 2006 Mesenchymal stem cells derived from human chorionic plate may promote hematopoietic differentiation of the human embryonic stem cell line SNUhES3. Acta Haematol 116:219-22
Kirschbaum S 1955 [Application of the amniotic membrane in extensive burns.]. Dia Med 27:1507-13
Koziak A, Marcheluk A, Dmowski T, Szczesniewski R, Kania P, Dorobek A 2004 Reconstructive surgery of male urethra using human amnion membranes (grafts)—first announcement. Ann Transplant 9:21-4
Marcus A J, Coyne T M, Rauch J, Woodbury D, Black I B 2008 Isolation, characterization, and differentiation of stem cells derived from the rat amniotic membrane. Differentiation 76:130-44
Marcus A J, Woodbury D 2008 Fetal stem cells from extraembryonic tissues: do not discard. J Cell Mol Med 12:730-42
Mhaskar R 2005 Amniotic membrane for cervical reconstruction. Int J Gynaecol Obstet 90:123-7
Miki T, Marongiu F, Ellis E, S C S 2007 Isolation of amniotic epithelial stem cells. Curr Protoc Stem Cell Biol Chapter 1: Unit 1E 3
Miki T, Strom S C 2006 Amnion-derived pluripotent/multipotent stem cells. Stem Cell Rev 2:133-42
Morton K E, Dewhurst C J 1986 Human amnion in the treatment of vaginal malformations. Br J Obstet Gynaecol 93:50-4
Park J H, Jeoung J W, Wee W R, Lee J H, Kim M K, Lee J L 2008 Clinical efficacy of amniotic membrane transplantation in the treatment of various ocular surface diseases. Cont Lens Anterior Eye 31:73-80
Perfil'Ev G N 1959 [Utilization of amniotic membranes for the treatment of burns.]. Eksp Khirurgiia 4:54-5
Pigeon J 1960 Treatment of second-degree burns with amniotic membranes. Can Med Assoc J 83:844-5
Sangwan V S, Burman S, Tejwani S, Mahesh S P, Murthy R 2007 Amniotic membrane transplantation: a review of current indications in the management of ophthalmic disorders. Indian J Opthalmol 55:251-60
Scheibe G 1966 [The amnion transplantation as a provisional skin substitute following burns]. Monatsschr Unfallheilkd Versicher Versorg Verkehrsmed 69:57-65
Soncini M, Vertua E, Gibelli L, Zorzi F, Denegri M, Albertini A, Wengler G S, Parolini O 2007 Isolation and characterization of mesenchymal cells from human fetal membranes. J Tissue Eng Regen Med 1:296-305
Srinivas S, Mavrikakis E, Jenkins C 2007 Amniotic membrane transplantation for painful bullous keratopathy. Eur J Opthalmol 17:7-10
Sterling J A 1956 Use of amniotic membranes to cover surface defects due to flame burns. Am J Surg 91:940-2
Tancer M L, Katz M, Veridiano N P 1979 Vaginal epithelialization with human amnion. Obstet Gynecol 54:345-9
Tejwani S, Kolari R S, Sangwan V S, Rao G N 2007 Role of amniotic membrane graft for ocular chemical and thermal injuries. Cornea 26:21-6
Zafar M, Saeed S, Kant B, Murtaza B, Dar M F, Khan N A 2007 Use of amnion in vaginoplasty for vaginal atresia. J Coll Physicians Surg Pak 17:107-9
Zubovich V S 1963 [Amniotic Membranes in the Treatment of Skin Burns in Children.]. Zdravookhr Beloruss 36:71-2

What is claimed is:

1. A device for sampling an amniotic membrane or chorionic membrane, the device comprising:
a first arm;
a second arm connected to the first arm;
a first handle connected to the first arm;
a second handle connected to the second arm;
a cutting element connected to the first arm;
a storage vessel connected to the second arm; and
a tissue support member connected to and covering an end of the storage vessel;
wherein:
at least one of the first and second arms is moveable between an open position of the device and a closed position of the device; and when the device is transitioned from the open position to the closed position, the cutting element cuts both a biological material comprising an amniotic membrane or chorionic membrane positioned between the first arm and the second arm and the tissue support member; and the cutting element deposits both the cut biological material and the cut tissue support member into the vessel.

2. The device of claim 1 wherein the storage vessel is removably connected to the second arm.

3. The device of claim 1 wherein the cutting element and the storage vessel are coaxially aligned when the device is in the closed position.

4. The device of claim 1 wherein the storage vessel is a sealable storage vessel, and wherein the device seals the storage vessel after the cut biological sample and tissue support member are deposited into the vessel.

5. The device of claim 1 further comprising a cap for sealing the storage vessel.

6. The device of claim 5 wherein the cutting element is integral with one of the following:
the storage vessel; and
the cap.

7. The device of claim 1 wherein the storage vessel holds a biological medium and the tissue support member retains the biological medium within the storage vessel.

8. The device of claim 1, further comprising a cassette connected to one of the first and second arms, wherein the cassette comprises at least one of the following:
a cap;
the storage vessel; and
the cutting element.

9. The device of claim 8 wherein the cassette further comprises additional storage vessels and corresponding additional cutting elements; and closing the device automatically advances the cassette.

10. The device of claim 9 wherein the cassette comprises a linear array of storage vessels or a circular or semicircular array of storage vessels.

11. The device of claim 8 wherein the cassette comprises the cutting element and the storage vessel.

12. The device of claim 8 wherein the cassette comprises the cap and the cutting element.

13. The device of claim 1 wherein the cutting element comprises a plurality of cutting elements and the storage vessel comprises a corresponding plurality of storage vessels, wherein closing the device results in cutting of a plurality of samples of the biological material and tissue support member by the plurality of cutting elements, and deposition of the plurality of samples and tissue support member in the corresponding plurality of storage vessels.

14. The device of claim 1 wherein the storage vessel comprises a tracking device selected from the group consisting of a barcode and a radio frequency identification tag.

15. A method of sampling an amniotic membrane or chorionic membrane comprising:

positioning a biological material comprising an amniotic membrane or chorionic membrane between the first arm and the second arm of the device of claim 1 in an open position; and closing the device such that a sample of the biological material and tissue support member are cut and deposited into the vessel.

16. The method of claim 15 comprising:

inserting a cassette comprising a plurality of storage vessels;

closing the device such that a sample of the biological material and tissue support member are cut and deposited into at least one of the vessels; and advancing the cassette to align an unused vessel.

17. The method of claim 15, wherein the cassette comprises a plurality of storage vessels and a corresponding plurality of cutting elements; and opening the device results in advancement of a storage vessel.

18. A kit for collecting and storing a sample of an amniotic membrane or chorionic membrane comprising the device of claim 1.

* * * * *